US009863902B2

(12) United States Patent
Giridhar et al.

(10) Patent No.: US 9,863,902 B2
(45) Date of Patent: Jan. 9, 2018

(54) MICROELECTRONIC FLUID DETECTOR

(71) Applicant: STMicroelectronics Asia Pacific Pte Ltd.

(72) Inventors: Archit Giridhar, Singapore (SG); Teck Khim Neo, Singapore (SG)

(73) Assignee: STMicroelectronics Asia Pacific Pte Ltd., Singapore (SG)

( * ) Notice: Subject to any disclaimer, the term of this patent is extended or adjusted under 35 U.S.C. 154(b) by 764 days.

(21) Appl. No.: 14/200,928

(22) Filed: Mar. 7, 2014

(65) Prior Publication Data
US 2015/0253271 A1 Sep. 10, 2015

(51) Int. Cl.
*G01N 27/07* (2006.01)
*G01F 22/00* (2006.01)

(52) U.S. Cl.
CPC ............ *G01N 27/07* (2013.01); *G01F 22/00* (2013.01); *Y10T 29/49165* (2015.01)

(58) Field of Classification Search
CPC ................................ G01F 22/00; G01N 27/07
See application file for complete search history.

(56) References Cited

U.S. PATENT DOCUMENTS

| 2010/0078753 | A1* | 4/2010 | Mehregany | G01F 1/6888 257/467 |
| 2012/0150004 | A1* | 6/2012 | Currie | A61B 5/1486 600/347 |
| 2012/0168882 | A1* | 7/2012 | Cherian | G01N 33/48785 257/414 |
| 2013/0302843 | A1* | 11/2013 | Son | G01N 27/02 435/29 |

OTHER PUBLICATIONS

Le Neel et al., "Flexible Electrochemical Micro-Sensor," U.S. Appl. No. 14/200,828, filed Mar. 7, 2014 (30 pgs.).

* cited by examiner

*Primary Examiner* — Jennifer Simmons
(74) *Attorney, Agent, or Firm* — Seed IP Law Group LLP

(57) ABSTRACT

A resistive microelectronic fluid sensor implemented as an integrated voltage divider circuit can sense the presence of a fluid within a fluid reservoir, identify the fluid, and monitor fluid temperature or volume. Such a sensor has biomedical, industrial, and consumer product applications. After fluid detection, the fluid can be expelled from the reservoir and replenished with a fresh supply of fluid. A depression at the bottom of the sample reservoir allows a residual fluid to remain undetected so as not to skew the measurements. Electrodes can sense variations in the resistivity of the fluid, indicating a change in the fluid chemical composition, volume, or temperature. Such fluctuations that can be electrically sensed by the voltage divider circuit can be used as a thermal actuator to trigger ejection of all or part of the fluid sample.

28 Claims, 12 Drawing Sheets

MICROELECTRONIC FLUID DETECTOR

BACKGROUND

Technical Field

The present disclosure relates to microelectronic fluid sensors on board integrated circuit chips.

Description of the Related Art

Fluids can be integrated with microelectronic circuitry in many applications including, for example, biomedical devices configured to perform physiological tests on samples of bodily fluids, and thermal actuators that eject fluid in response to changes in temperature.

Approximately 25-30 million people in the United States are diagnosed with type II diabetes requiring monitoring of blood glucose at least twice daily. A common example of a biosensor device that relies on a microelectronic fluid sensor is a disposable test strip used for measurement of blood glucose levels in diabetic patients as shown in FIG. 1. A typical blood glucose monitoring apparatus 80 includes a conventional disposable strip biosensor 82 and a portable electronic monitor 83. The biosensor 82 is made of a semi-rigid backing material 84 approximately an inch long, impregnated with an electrolytic chemical reagent 86 at one end and printed with electrodes 88 at the other end. The patient pricks a fingertip, applies a blood sample 89 to the electrolytic chemical reagent 86, and inserts the electrodes 88 into the portable electronic monitor 83. The electrolytic chemical reagent 86 conducts a current that is proportional to an amount of glucose in the blood sample 89. Current flow conducted via the electrodes 88 in the biosensor 82 closes a circuit when the biosensor 82 is inserted into the portable electronic monitor 83. The current in the circuit can then be measured by the portable electronic monitor 83. The portable electronic monitor 83 is configured with software that converts the current measurement into a numerical value that represents the blood glucose level. The portable electronic monitor 83 then provides a digital readout of the numerical value and stores the numerical value as blood glucose data in an electronic memory. By either recording or downloading the blood glucose data, the patient can track blood glucose values over time to adjust insulin dosage.

Use of an impregnated biosensor strip is problematic for several reasons. The chemical reagent 86 may degrade over time such that the biosensor strip has a finite shelf life and must be stamped with an expiration date. In addition, this type of biosensor strip is expensive, and available only on a prescription basis, as opposed to being an item that is sold over-the-counter. When the liquid sample is applied, sometimes the strip fails to take up enough of the liquid volume to make an accurate reading, and the test must be repeated, which incurs even more expense. Finally, the strips are disposable and cannot be re-used.

Another type of fluid detector that can be used to detect electrical properties of a fluid sample such as the blood sample 89, uses an open fluid reservoir instead of an impregnated reagent. An example of such a detector is a capacitive fluid detector as shown and described below with respect to FIGS. 2A, 3A, and 3B. Such a capacitive fluid detector transmits electrical signals through the fluid sample in the reservoir. The electrical signals can be compared against previous signals or an independent standard to detect changes. Changes in the electrical signals can indicate the presence or absence of fluid in a region between two electrodes, for example. Once presence of the fluid sample is detected, further changes in such signals can indicate fluctuating levels of fluid components that are charge-dependent such as glucose, electrolytes, or ions such as calcium, magnesium, potassium, and the like. The electrical signal data can then be sent to a microprocessor to calculate corresponding electrical properties of the fluid sample.

Depending on the design of the sensor, such a capacitive detection system may provide information regarding the presence of fluid, or the presence of certain components within the fluid, but not necessarily information regarding an amount of fluid present. For example, if the fluid participates in the circuit as part of a capacitive electrode rather than part of a capacitive dielectric, the capacitor geometry may not allow distinguishing between a small volume of fluid and a large volume. In the parallel plate capacitor sensor described above, the fluid is typically incorporated as a portion of one of the electrodes. However, where the fluid is incorporated as the dielectric, or a portion of the dielectric, it becomes possible to identify the fluid based on the dielectric constant. Such an arrangement is not feasible in the case of a capacitive sensor, however, because the dielectric, being sandwiched between two metal plates, is not easily accessible for introduction of a fluid sample by a user. Furthermore, capacitive sensor measurements may be affected by parasitic capacitances elsewhere in the circuit that are not actually related to the fluid sample and can therefore skew the test results. For at least these reasons, it may be desirable to have other types of fluid sensors available on an integrated circuit chip in addition to, or in place of, capacitive fluid sensors.

BRIEF SUMMARY

A resistive microelectronic fluid detection system can determine more information about a fluid than a typical capacitive fluid detector can, and with greater accuracy, in part because the resistive fluid detector is not subject to parasitic effects. In addition to sensing the presence of a fluid in a reservoir, a resistive microelectronic fluid sensor can identify the fluid and determine its volume.

Embodiments of a resistive microelectronic fluid detector can be built so as to include a fluid reservoir that is at least partially exposed. An electrical signal can then be applied laterally across the fluid reservoir. Presence or absence of a fluid can then be determined directly and with less influence from external factors, for example, by applying a voltage and measuring whether or not a current flows through the sample reservoir. If a current flows and closes the circuit, it can be deduced that a sample is present. In one embodiment of a resistive microelectronic fluid detector, the bottom of the sample reservoir is modified with a depression so that a certain volume of fluid can be present without conducting the electrical signal. Using such a modified reservoir, when a signal is detected, it is known that the volume of the sample is above a certain threshold value.

In another embodiment, if a second resistor is constructed adjacent to the fluid reservoir, simple equations for a voltage divider circuit allow determination of the fluid sample volume if the fluid resistivity is known. Conversely, identification of the fluid is possible if the volume of the sample is known.

In another embodiment, the sample reservoir can be extended vertically and capped to form a partially or substantially enclosed chamber within a microfluidic ejection system. In such a system, detection of a threshold volume of fluid within the reservoir can trigger ejection of the fluid sample out of the chamber, through a nozzle in the cap. Electrodes contacting the fluid within the reservoir can further be used to sense differences or variation in the resistivity of the fluid, indicating a different type of fluid is present, or a change in the fluid chemical composition or the fluid volume. In some applications, for example, changes in resistivity of the fluid can indicate temperature fluctuations. Such fluid characteristics that can be electrically sensed by a voltage divider circuit can in turn be used as a thermal actuator to trigger ejection of all or part of the fluid sample.

The fluid detector described herein may be used in conjunction with a universal flexible micro-sensor as described in U.S. Patent Publication No. 2015/0253276.

BRIEF DESCRIPTION OF THE SEVERAL VIEWS OF THE DRAWINGS

In the drawings, identical reference numbers identify similar elements. The sizes and relative positions of elements in the drawings are not necessarily drawn to scale.

DETAILED DESCRIPTION

Figure 1:
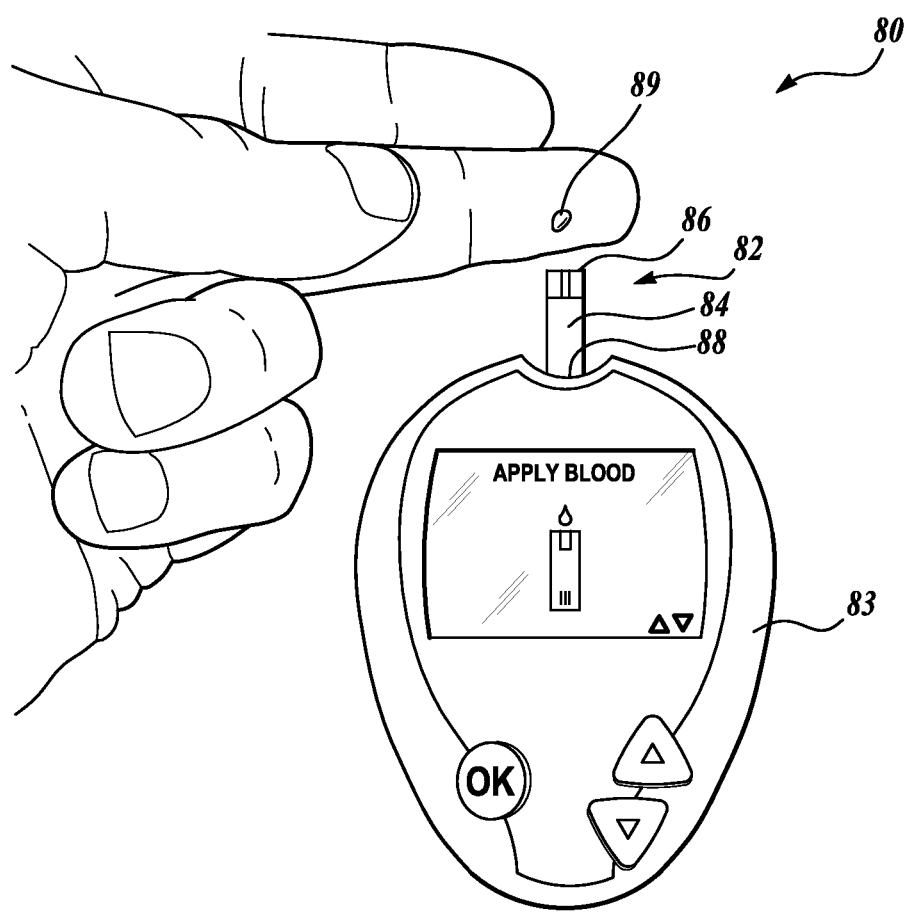
FIG. 1 is a pictorial view of a typical blood glucose monitoring system that employs a test strip impregnated with an electrolytic chemical reagent, as found in the prior art.

In the following description, certain specific details are set forth in order to provide a thorough understanding of various aspects of the disclosed subject matter. However, the disclosed subject matter may be practiced without these specific details. In some instances, well-known structures and methods of semiconductor processing comprising embodiments of the subject matter disclosed herein have not been described in detail to avoid obscuring the descriptions of other aspects of the present disclosure.

Unless the context requires otherwise, throughout the specification and claims that follow, the word "comprise" and variations thereof, such as "comprises" and "comprising" are to be construed in an open, inclusive sense, that is, as "including, but not limited to."

Reference throughout the specification to "one embodiment" or "an embodiment" means that a particular feature, structure, or characteristic described in connection with the embodiment is included in at least one embodiment. Thus, the appearance of the phrases "in one embodiment" or "in an embodiment" in various places throughout the specification are not necessarily all referring to the same aspect. Furthermore, the particular features, structures, or characteristics may be combined in any suitable manner in one or more aspects of the present disclosure.

Reference throughout the specification to integrated circuits is generally intended to include integrated circuit components built on semiconducting substrates, whether or not the components are coupled together into a circuit or able to be interconnected. Throughout the specification, the term "layer" is used in its broadest sense to include a thin film, a cap, or the like and one layer may be composed of multiple sub-layers.

Reference throughout the specification to conventional thin film deposition techniques for depositing silicon nitride, silicon dioxide, metals, or similar materials include such processes as chemical vapor deposition (CVD), low-pressure chemical vapor deposition (LPCVD), metal organic chemical vapor deposition (MOCVD), plasma-enhanced chemical vapor deposition (PECVD), plasma vapor deposition (PVD), atomic layer deposition (ALD), molecular beam epitaxy (MBE), electroplating, electro-less plating, and the like. Specific embodiments are described herein with reference to examples of such processes. However, the present disclosure and the reference to certain deposition techniques should not be limited to those described. For example, in some circumstances, a description that references CVD may alternatively be done using PVD, or a description that specifies electroplating may alternatively be accomplished using electro-less plating. Furthermore, reference to conventional techniques of thin film formation may include growing a film in situ. For example, in some embodiments, controlled growth of an oxide to a desired thickness can be achieved by exposing a silicon surface to oxygen gas or to moisture in a heated chamber.

Reference throughout the specification to conventional photolithography techniques, known in the art of semiconductor fabrication for patterning various thin films, includes a spin-expose-develop process sequence typically followed by an etch process. Alternatively or additionally, photoresist can also be used to pattern a hard mask (e.g., a silicon nitride hard mask), which, in turn, can be used to pattern an underlying film.

Reference throughout the specification to conventional etching techniques known in the art of semiconductor fabrication for selective removal of polysilicon, silicon nitride, silicon dioxide, metals, photoresist, polyimide, or similar materials includes such processes as wet chemical etching, reactive ion (plasma) etching (RIE), washing, wet cleaning, pre-cleaning, spray cleaning, chemical-mechanical planarization (CMP) and the like. Specific embodiments are described herein with reference to examples of such processes. However, the present disclosure and the reference to certain deposition techniques should not be limited to those described. In some instances, two such techniques may be interchangeable. For example, stripping photoresist may entail immersing a sample in a wet chemical bath or, alternatively, spraying wet chemicals directly onto the sample.

Specific embodiments are described herein with reference to microelectronic fluid sensors and fluid ejection devices that have been produced; however, the present disclosure and the reference to certain materials, dimensions, and the details and ordering of processing steps are exemplary and should not be limited to those shown.

Figure 2B:
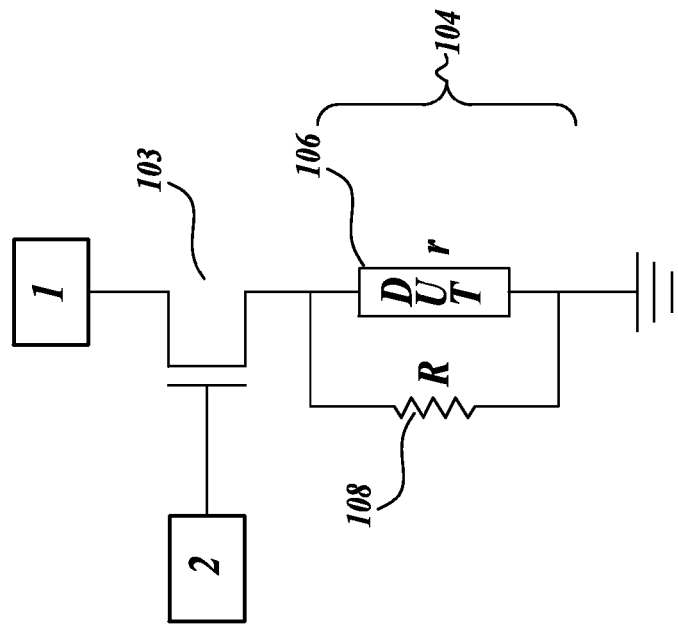
FIG. 2B is a schematic of a resistive microelectronic fluid detector, as described herein, according to one embodiment.
Figure 2A:
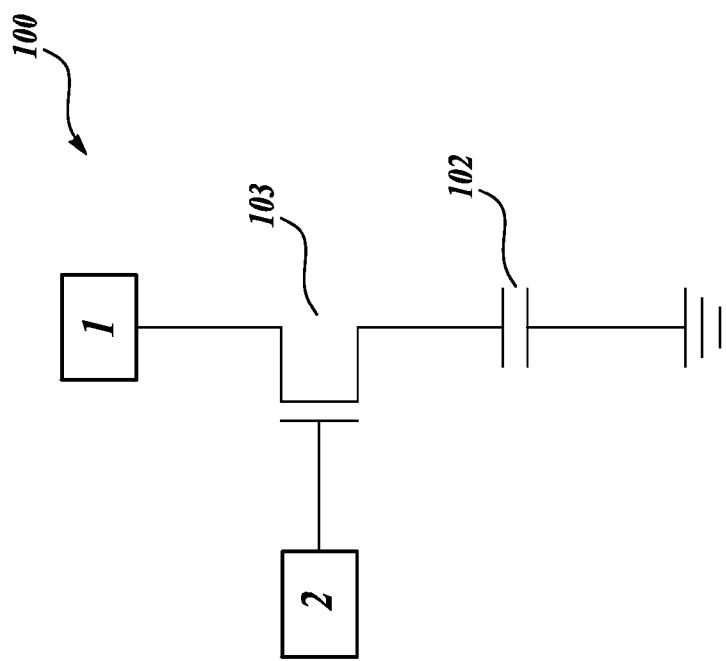
FIG. 2A is a schematic diagram of a circuit that includes a conventional capacitive fluid sensor, according to the prior art.

FIG. 2A shows a fluid detection circuit 100 that provides context for a conventional capacitive fluid sensor 102, according to the prior art. When nodes 1 and 2 are energized, a transistor 103 turns on and applies a signal to the conventional capacitive fluid sensor 102. The capacitance value is sensed and this provides an indication of the fluid being tested.

FIG. 2B shows a resistive microelectronic fluid detector 104, as described herein, that is proposed to replace the conventional capacitive fluid sensor 102, for example, adjacent to nodes 1 and 2 in the circuit 100. In one embodiment, the resistive microelectronic fluid detector 104 is in the form of a voltage divider that includes a device under test (DUT) 106 coupled in parallel to a known reference device 108 having a resistance R that is much larger than the resistance r of the DUT 106. For example, R can be on the order of 10-100 k$\Omega$, while r can vary over a range of a very high value (several G$\Omega$ or higher) when the fluid under test is not present, to a lower value, such as approximately 1 k$\Omega$ when the fluid under test is present.

Figure 3:
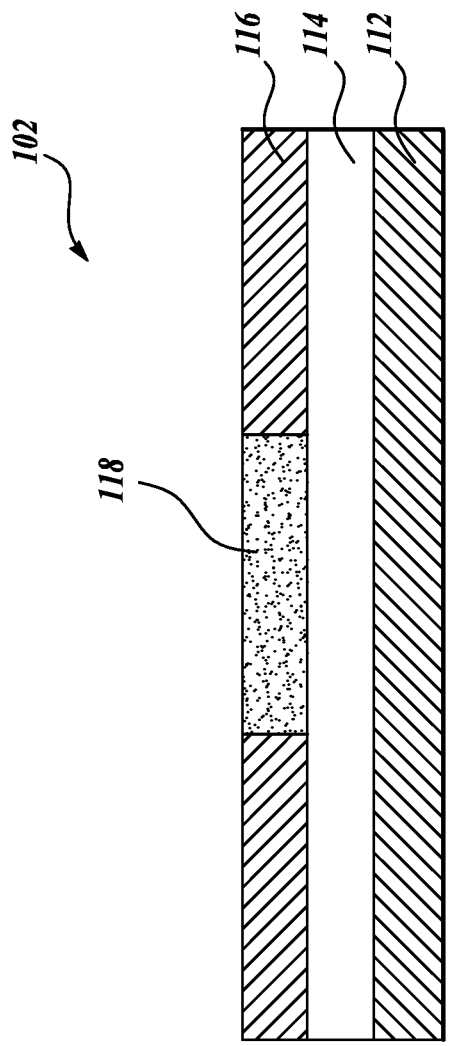
FIG. 3 is a cross-sectional view of an integrated circuit implementation of a conventional capacitive fluid sensor.

FIG. 3 shows an integrated circuit embodiment of the conventional capacitive fluid sensor 102. The integrated capacitive fluid sensor 102 is in the form of a parallel plate capacitor that includes a bottom electrode 112, a dielectric 114, and a top electrode 116. The bottom and top electrodes 112 and 116 are generally metallic while the dielectric 114 can be made of a passivation material or another dielectric available in a semiconductor fabrication process such as an inter-layer dielectric (ILD) material. The top electrode 116 includes a fluid reservoir 118 intended to contain a volume of electrolytic fluid under test, for example, a blood sample, a DNA sample, an industrial chemical sample, or the like. The electrical conductivity of the fluid sample in the fluid reservoir 118 is thus exploited to engage the fluid sample as an integral part of the top electrode 116 of the parallel plate capacitor. If the fluid reservoir 118 is empty, the capacitance of the parallel plate capacitor will be reduced proportionally, according to the relationship C=KA/d, wherein A is the surface area of the top electrode 116, K is the dielectric constant of the dielectric 114, and d is the thickness of the dielectric 114. When the fluid reservoir 118 is empty, the electrode surface area A is reduced. Therefore, the presence or absence of fluid in the fluid reservoir 118 is detectable by the conventional integrated capacitive fluid sensor 102. However, information regarding an amount of fluid present in the fluid reservoir 118 is not provided by such a conventional capacitive sensor.

A microelectronic fluid detector 104, as described herein, is realized as a miniature integrated voltage divider circuit that is proposed as a substitute sensor to use in place of the conventional integrated capacitive fluid sensor 102. The integrated circuit voltage divider includes a known reference element (R) in the form of a resistive thin film layer, and an unknown resistance in the form of a fluid reservoir 126 (r), positioned between two electrodes. The resistance r varies with changes in the fluid present in the reservoir 126.

Two embodiments of such an integrated circuit voltage divider, 104a and 104b, are presented herein in FIGS. 4B and 4C, and FIGS. 6B and 6C, respectively. FIG. 4A reproduces the schematic representation of the voltage divider. FIG. 4A is shown for comparison against the top plan view shown in FIG. 4B and the cross-sectional view shown in FIG. 4C. During operation of the resistive microelectronic fluid detector 104, an electrical signal is applied at electrodes 120 and 122 to test a fluid sample, which is the device under test 106.

Figure 4:
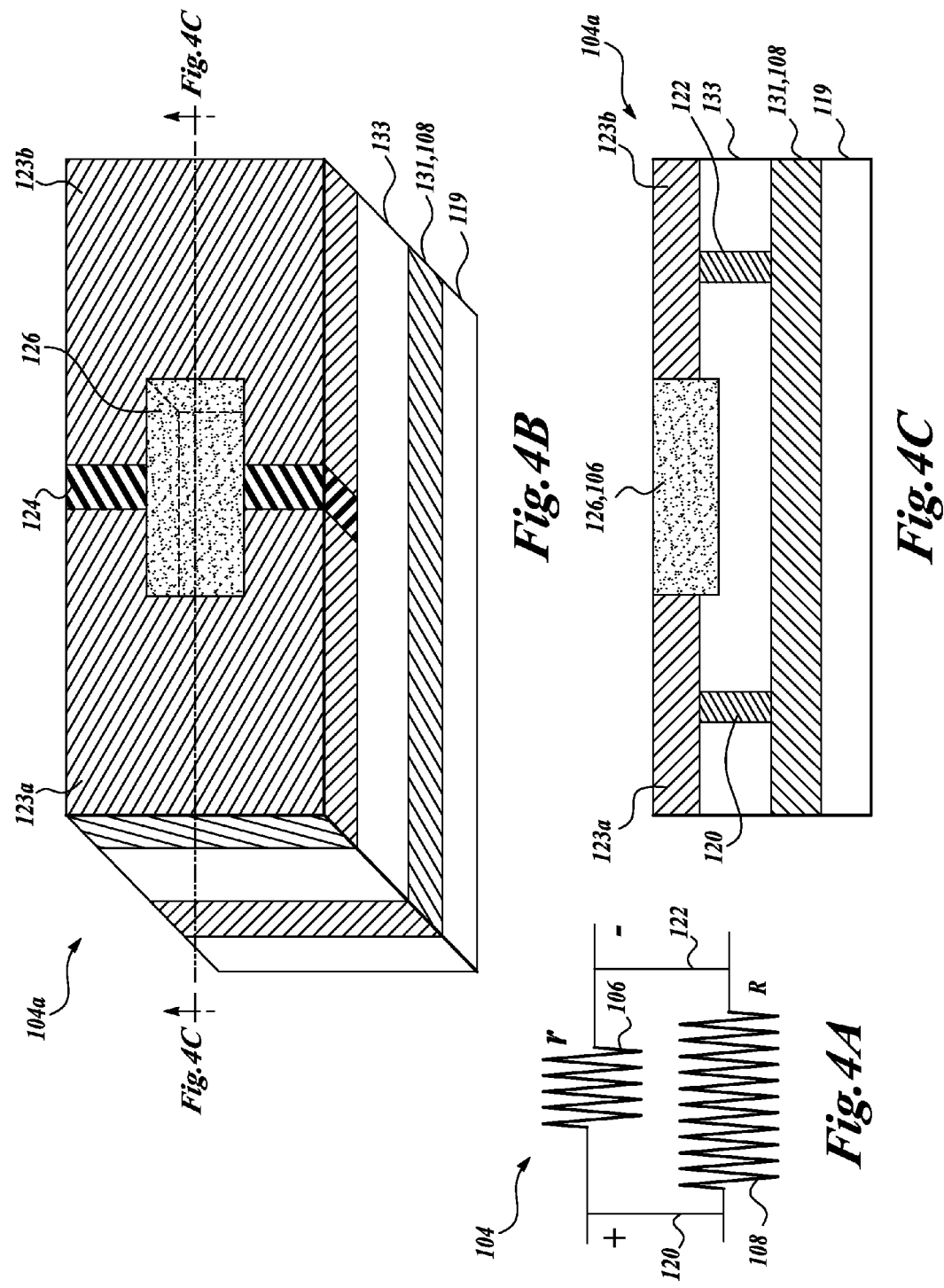
FIG. 4A is a schematic of a resistive microelectronic fluid detector in the form of a voltage divider circuit element that includes a device under test and a known reference device.
FIG. 4B is a top perspective view of a first integrated circuit embodiment of the microelectronic fluid detector shown in FIG. 4A.
FIG. 4C is a cross-sectional view of a first integrated circuit embodiment of the microelectronic fluid detector shown in FIG. 4B, taken along the vertical cut line A-A' through the center of the fluid reservoir.
Figure 5:
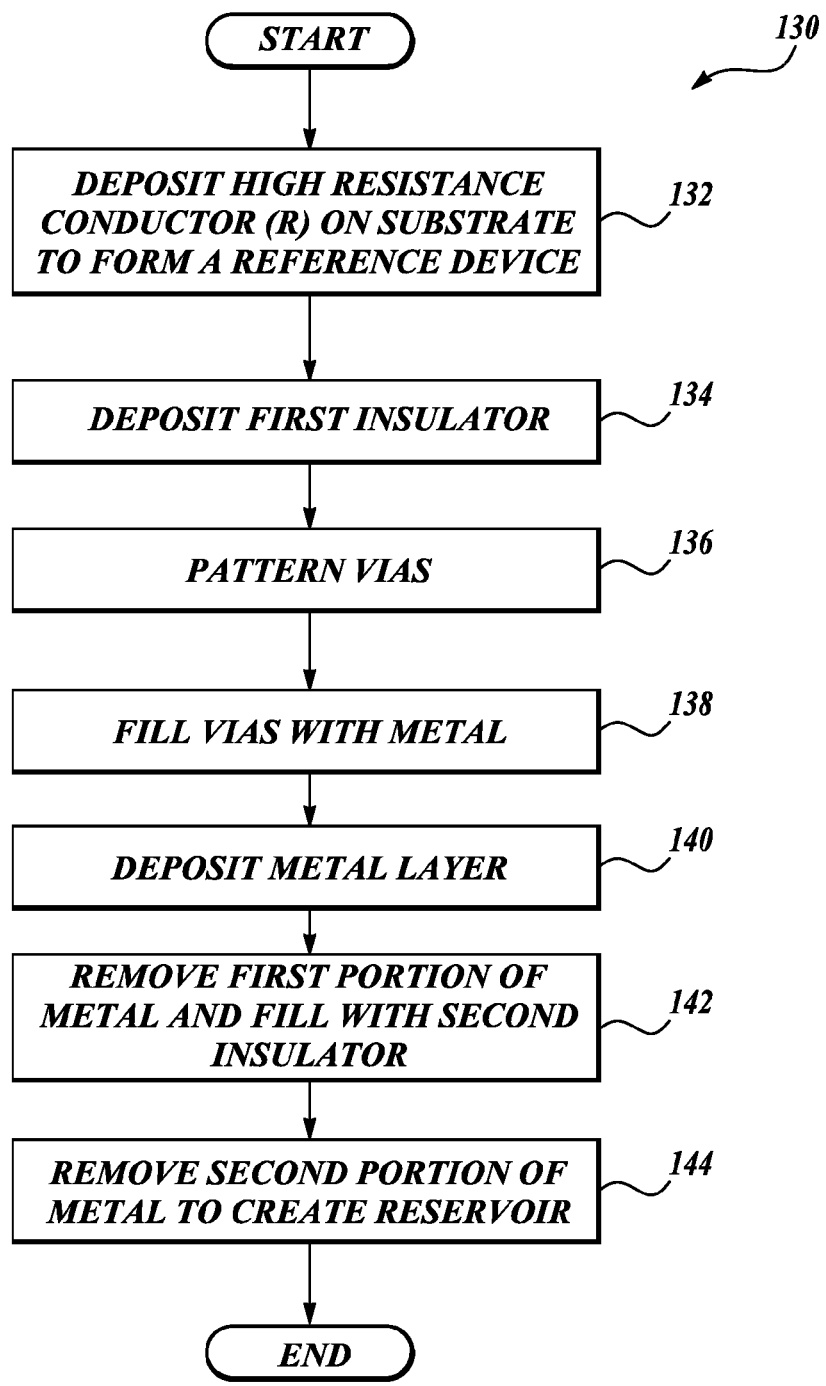
FIG. 5 is a flow diagram of a method of making the first integrated circuit microelectronic fluid detector shown in FIGS. 4B and 4C.

FIGS. 4B and 4C show different views of the first embodiment 104a of the microelectronic fluid detector 104. With reference to FIGS. 4B and 4C, the first embodiment 104a is one integrated circuit implementation of the resistive microelectronic fluid detector 104. The first embodiment 104a of the voltage divider circuit 104 includes a high resistance material 131 as the reference device (R) and a fluid reservoir 126 as the resistor r. The two resistors are coupled by electrodes 123a and 123b, and by vias 120 and 122 through a first insulator 133. A second insulator 124 separates the electrodes 123a and 123b so that they are laterally spaced apart from one another, and can be coupled through the fluid in the reservoir 126. The first embodiment 104a can be built on a semiconductor substrate 119, according to steps in an exemplary method 130, as shown in FIG. 5. Alternatively, the substrate 119 can be an insulator, such as a polymer layer, a polyimide layer, a glass layer, or the like.

At 132, a high resistance material 131 that serves as the reference device 108 is formed overlying the substrate 119. In one embodiment, the high resistance material 131 is a high resistance conductor such as silicon carbide (SiC). The high resistance material 131 could also be a lightly doped polysilicon or other high resistance material. In other embodiments, the material serving as the reference device 108 can be a passivation material such as a doped or conductive polyimide that can be spun onto the substrate in liquid form. Alternatively, another insulator with some conductive properties can be deposited using a conventional thin film deposition process.

At 134, the first insulator 133 is formed on top of the high resistance material 131 by depositing an inter-layer dielectric (ILD) material such as, for example, silicon dioxide (SiO$_2$) using a conventional thin film deposition process.

At 136, vias are patterned in the first insulator 133 using a conventional photolithography and etching process sequence.

At 138, the vias are filled with metal to form coupling wires 120 and 122.

At 140, a metal layer is deposited on top of the first insulator 133. The metal layer can be made of copper, silver, platinum, gold, titanium, tungsten, and the like, or alloys thereof.

At 142, a first portion of the metal layer is removed and filled with a second insulator 124 as shown in FIG. 4B, thus creating electrodes 123a and 123b. The second insulator 124 can be made from an oxide or nitride material, for example. If the height of the second insulator 124, as deposited, exceeds that of the electrodes, the top surface of the device can be planarized by polishing the insulator material and stopping on the surface of the electrodes. Otherwise, the electrodes can be polished to stop on the second insulator 124. The second insulator 124 ensures that the electrodes 123a, 123b remain spaced apart from one another so that an applied signal will be conducted through the fluid sample as the device under test 106, and not be short-circuited between the electrodes 123a, 123b.

At 144, a second portion of the metal layer is removed, for example by etching, to create a fluid reservoir 126. Thus, the electrodes 123a, 123b and the second insulator 124 together form walls that bound the fluid reservoir 126 on four sides, while the first insulator 133 forms a floor that bounds the fluid reservoir 126 from below. The reservoir 126 can extend below the dielectric-metal interface, into the first insulator 133 in one embodiment, but this is not required.

The second embodiment 104b of the voltage divider circuit 104 also includes a high resistance material 131 as the reference device (R) and a fluid reservoir 126 as the resistor r. The two resistors are coupled by electrodes 120 and 122 which are formed with lower portions 120a and 122a on either side of the reference device R and upper portions 120b and 122b on either side of the fluid reservoir 126 (r). The second insulator separates the upper portions of the electrodes 120b and 122b so that they are laterally spaced apart from one another, and can be coupled through the fluid in the reservoir 126.

Figure 6:
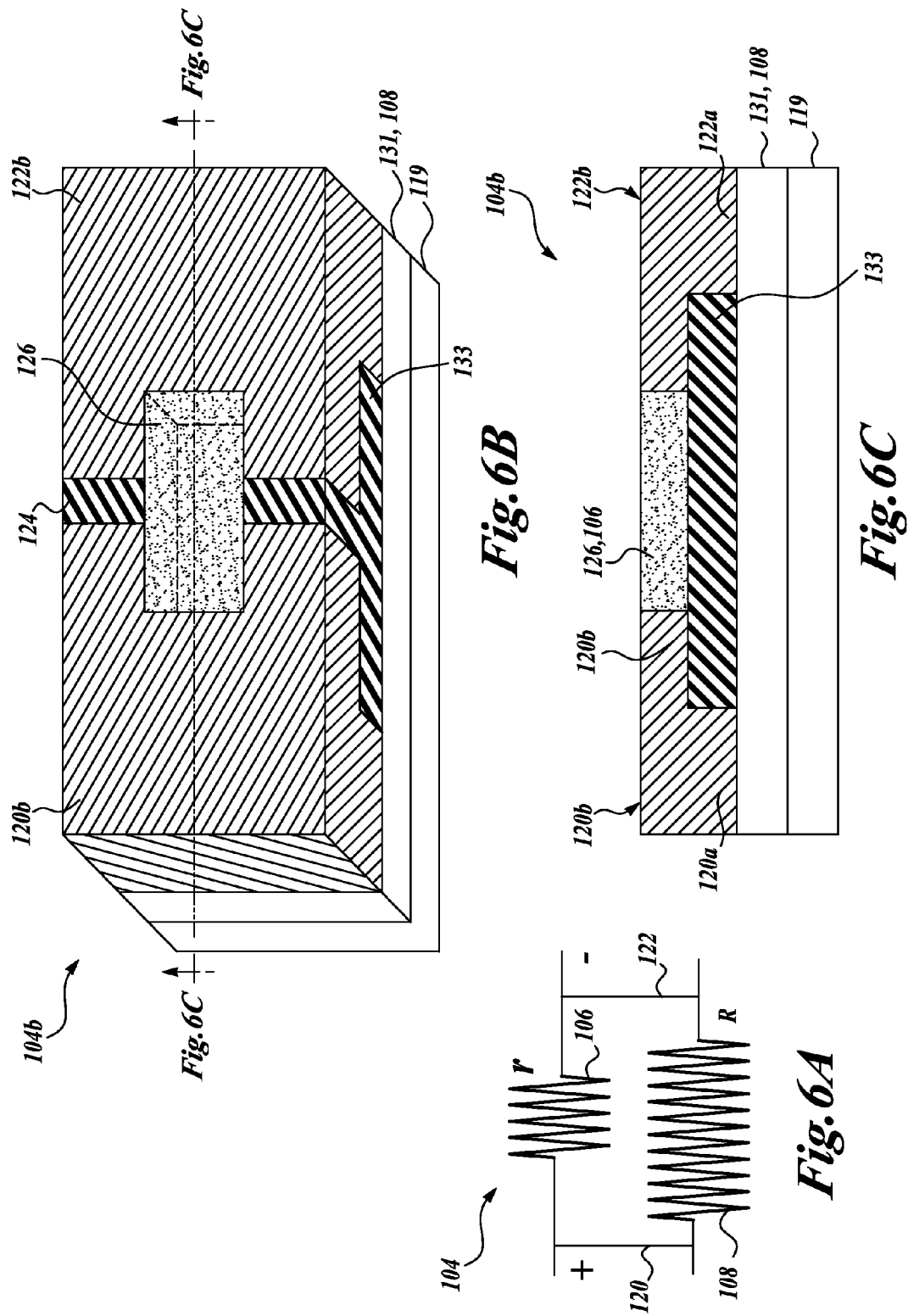
FIG. 6A reproduces the schematic diagram of the voltage divider circuit element shown in FIG. 4A.
FIG. 6B is a top perspective view of a second integrated circuit embodiment of the microelectronic fluid detector shown in FIG. 6A.
FIG. 6C is a cross-sectional view of a second integrated circuit embodiment of the microelectronic fluid detector shown in FIG. 6B, taken along the vertical cut line A-A' through the center of the fluid reservoir.
Figure 7:
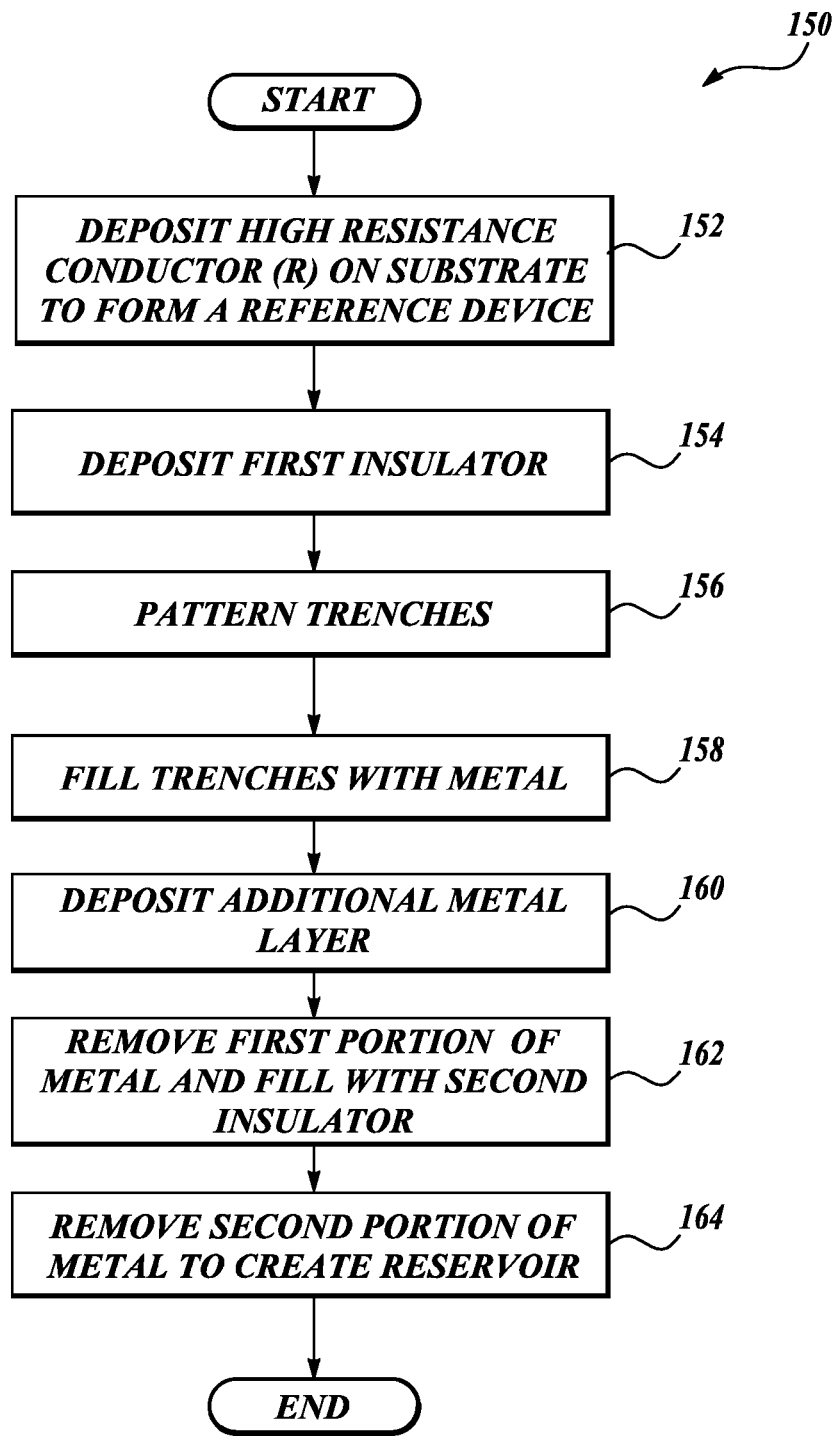
FIG. 7 is a flow diagram of a method of making the second integrated circuit microelectronic fluid detector shown in FIGS. 6B and 6C.

FIG. 6A reproduces the schematic representation of the resistive microelectronic fluid detector 104 in the form of a voltage divider that is proposed as a substitute sensor to use in place of the conventional integrated capacitive fluid sensor 102. FIG. 6A is provided for comparison against the top plan view shown in FIG. 6B and a cross-sectional view shown in FIG. 6C of a second embodiment 104b of the resistive microelectronic fluid detector 104. The second embodiment 104b can be built on the substrate 119, according to a method 150, as shown in FIG. 7.

At 152, a high resistance material 131 that serves as the reference device 108 is formed on top of the substrate 119, using a conventional thin film deposition process. In one embodiment, the reference device 108 has such a high resistance R, it conducts little to no current and, thus, could be considered an open circuit. In other embodiments, the reference device 108 is a high resistance conductor, such as SiC or lightly doped polysilicon.

At 154, a first insulator 133 is formed in contact with the high resistance material 131.

At 156, trenches are patterned in the first insulator 133 using a conventional photolithography and etching process sequence, to create an insulator block that provides vertical separation between the device under test 106 from the reference device 108.

At 158, the trenches are filled with metal to form lower portions of the electrodes, 120a and 122a, shown in FIG. 6C.

At 160, an additional metal layer is deposited on top of the filled trenches which will form upper portions of the electrodes 120b and 122b, shown in FIG. 6C.

At 162, a first portion of the additional metal layer is removed and filled with a second insulator 124. The second insulator 124 can be made from the same material as the first insulator 133, or it can be made of a different material. If the height of the second insulator 124, as deposited, exceeds that of the electrodes, the top surface of the device can be planarized by polishing the second insulator 124 and stopping on the upper portions of the electrodes 120b, 122b. Otherwise, the electrodes can be polished to stop on the second insulator 124. The second insulator 124 ensures that the electrodes 120b, 122b remain spaced apart from one another so that an applied signal will be conducted through the fluid sample as the device under test 106, and not be short-circuited between the electrodes.

At 164, a second portion of the metal layer is removed to create the fluid reservoir 126. Thus, the electrodes 120b, 122b and the second insulator 124 together form walls that bound the fluid reservoir 126 on four sides, while the high resistance material 131 forms a floor that bounds the fluid reservoir 126 from below.

Figure 8:
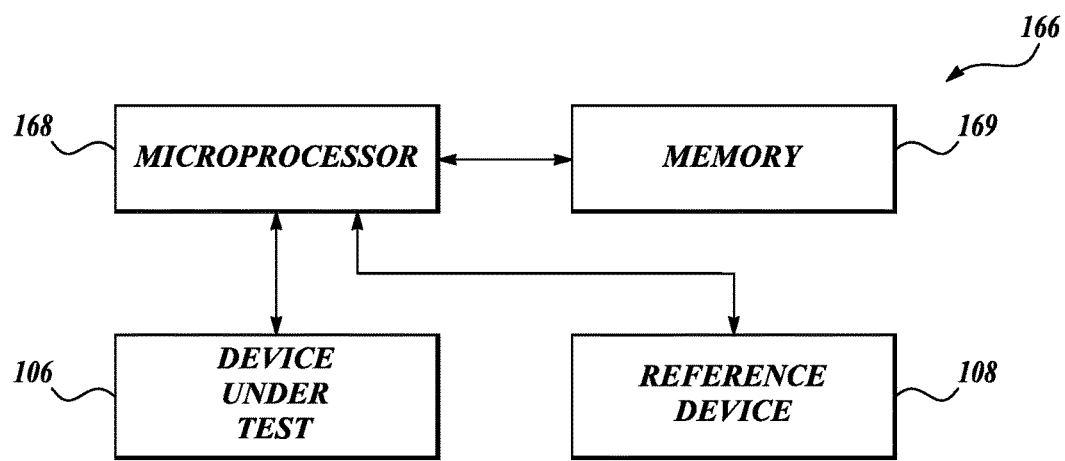
FIG. 8 is a block diagram of a microelectronic fluid sensor system as described herein.

FIG. 8 shows a microelectronic fluid sensor system 166 including a microprocessor 168 and an electronic memory 169, both of which can be located on the same integrated circuit chip as the microelectronic fluid detector 104 that includes the device under test 106 and the reference device 108. The electronic memory 169 stores instructions for execution by the microprocessor 168 to test fluid samples. In addition, the electronic memory 169 stores other data such as, for example, material information including resistivity values, material constants, and the like to support calculations such as those described herein.

There are two alternative embodiments to use for the substrate 119 when it takes the form of a semiconductor substrate. In a first embodiment, the semiconductor substrate 119 has, in addition to a foundation of a semiconductor substrate layer, electronic circuits formed therein. Such electronic circuits include transistors having source and drain regions and electrical interconnections coupling them to form logic gates. In this embodiment, the microprocessor, memory and other electronic circuits are formed in the semiconductor substrate 119, as well as numerous other layers overlying the semiconductor substrate 119 itself which are not specifically shown in FIGS. 4B and 4C. For example, there will be numerous interconnect metal layers and insulating layers which overlay the transistors formed in the substrate itself. Accordingly, reference to the semiconductor substrate 119 includes such integrated circuits as a whole, that is to say, the transistors and the interconnect layers connecting them. The numerous layers making up the transistors and the interconnect structure are omitted herein for ease of reference, and it is well understood by those of skill in art how to build an integrated circuit overlying a semiconductor substrate 119.

According to one embodiment, the high resistance material 131 will be one of the top most metal layers of the integrated circuit which overlays the semiconductor substrate 119. The various insulating and metal interconnect layers which form the microprocessor are formed on a different part of the die than that section shown in FIG. 4C and, thus, are not shown for ease in illustration. In most embodiments, there will be an insulating layer positioned between the conductive high resistance material 131 and the semiconductor substrate 119 itself and, as just explained herein, there may be numerous alternating conductive and insulating layers which electrically isolate the high resistance material 131 from the semiconductor substrate itself.

In an alternative embodiment, the substrate 119 is composed of a fully insulating material instead of being a semiconductor substrate. For example, the substrate 119 may be a polymer, a polyimide film or other supporting substrate which is capable of having a high resistance material 131 formed thereon. One technique by which the sensor 104 can be formed in which the substrate 119 is a polymer layer is described in U.S. patent application Ser. No. 14/200,828, incorporated herein by reference in its entirety.

Figure 9:
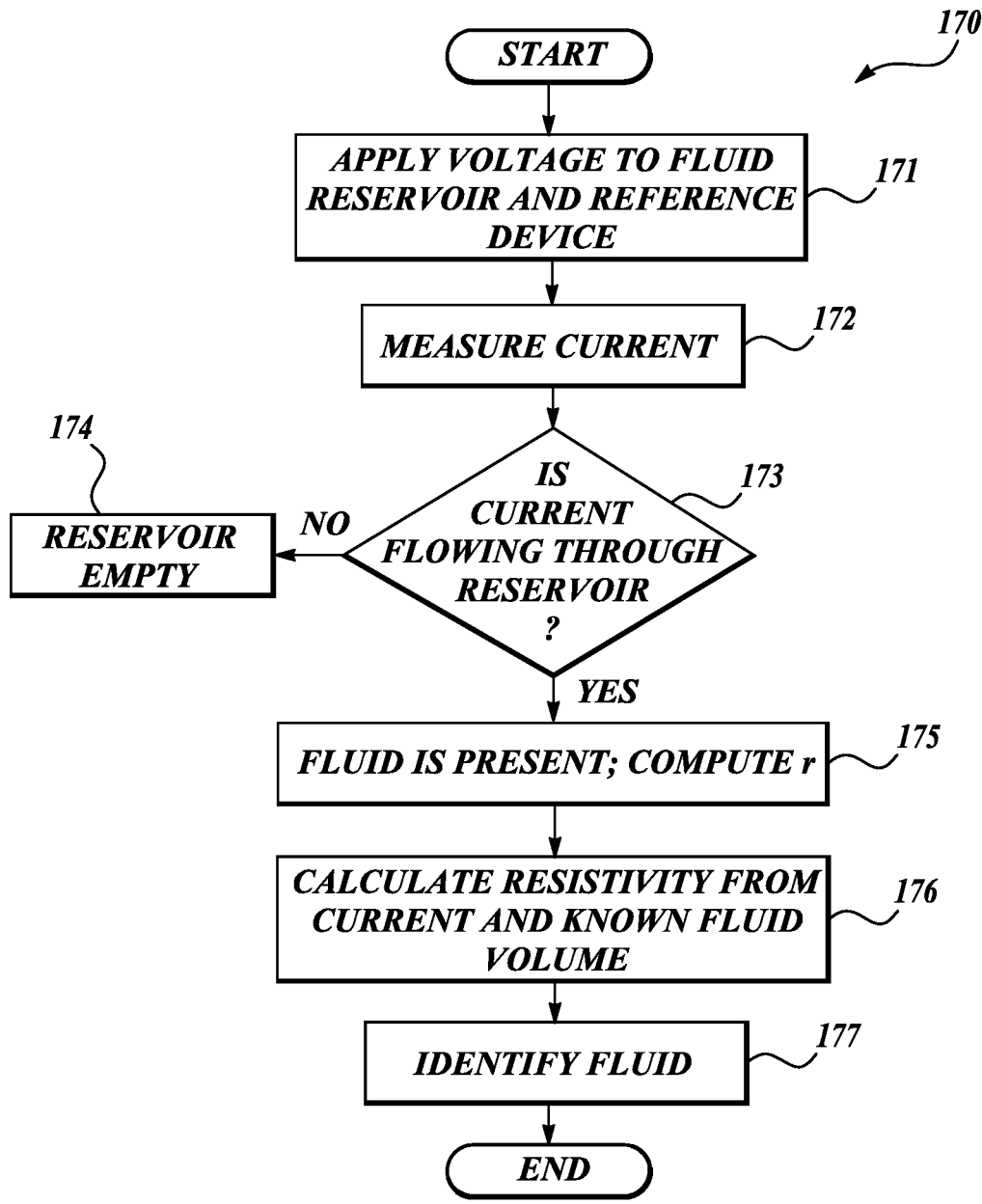
FIG. 9 is a flow diagram of a method of operating an integrated circuit microelectronic fluid detector to identify a fluid.

FIG. 9 shows steps carried out by the microprocessor 168 in an exemplary method 170 of operating the microelectronic fluid detector 104, according to one embodiment.

At 171, the fluid reservoir 126 is tested by applying an electrical signal to the voltage divider. For example, a voltage can be applied between electrodes 120 and 122 by coupling a power source to the electrodes 120 and 122.

At 172, a current is measured between the electrodes 120 and 122. If the fluid reservoir 126 is empty, all the current will flow through the reference device 108, according to the relationship $$I=V_{applied}/R, \qquad (1)$$

and no current will flow through the resistor r, which is the fluid reservoir 126. On the other hand, when the fluid reservoir 126 contains a fluid sample, the total electric current is divided so that some current flows through each of the fluid reservoir 126 ($r$) and the insulator block (R). The total current is thus given by $$I=V_{applied}(1/R+1/r) \qquad (2)$$

At 173, based on the measured value of I, it is determined by the microprocessor whether or not a current is flowing through the fluid reservoir.

At 174, if a current is flowing through the reservoir, it is concluded that a fluid is present in the fluid reservoir 126.

At 175, given that a fluid is present in the fluid reservoir 126, the resistance of the fluid sample, r, can be computed from equation (2) above, wherein V is applied, I is measured, and R is a known resistance that can be computed from the known geometry and material parameters of the high resistance material 131.

At 176, since the geometry of the fluid reservoir 126 is known, a resistivity, $\rho$, of the fluid sample can be calculated according to the well-known relationship $$r=\rho L/A \qquad (3)$$

wherein A is a surface area of the reservoir transverse to the direction of current flow, and L is the length of the reservoir. It is assumed, in the present embodiment, that the fluid sample substantially fills the reservoir 126.

At 177, once the resistivity is known, a lookup table of various material parameters stored in the electronic memory 169 can be consulted to identify the type of fluid present in the fluid reservoir 126.

Figure 10:
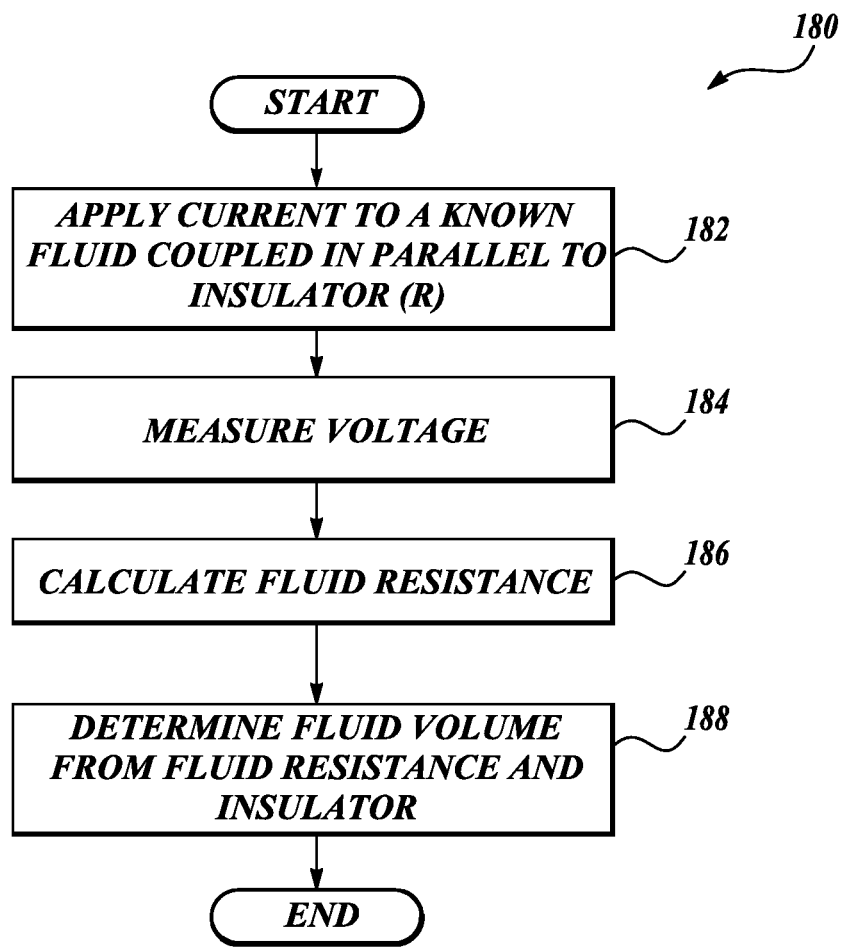
FIG. 10 is a flow diagram of a method of operating an integrated circuit microelectronic fluid detector to determine a fluid volume.

If the type of fluid is known, FIG. 10 shows steps carried out by the microprocessor 168 in an exemplary method 180 of operating the microelectronic fluid detector 104, to determine fluid volume of a known fluid sample, according to one embodiment.

At 182, an electric current is applied to the microelectronic fluid detector 104, wherein the fluid reservoir 126 contains a sample of an identified fluid.

At 184, a voltage is measured across the fluid reservoir 126.

At 186, the resistance, r, of the fluid sample is computed from equation (2).

At 188, the volume of the fluid sample is computed as V=AL wherein A is known and L is determined from equation (3).

Figures 11A, 11B:
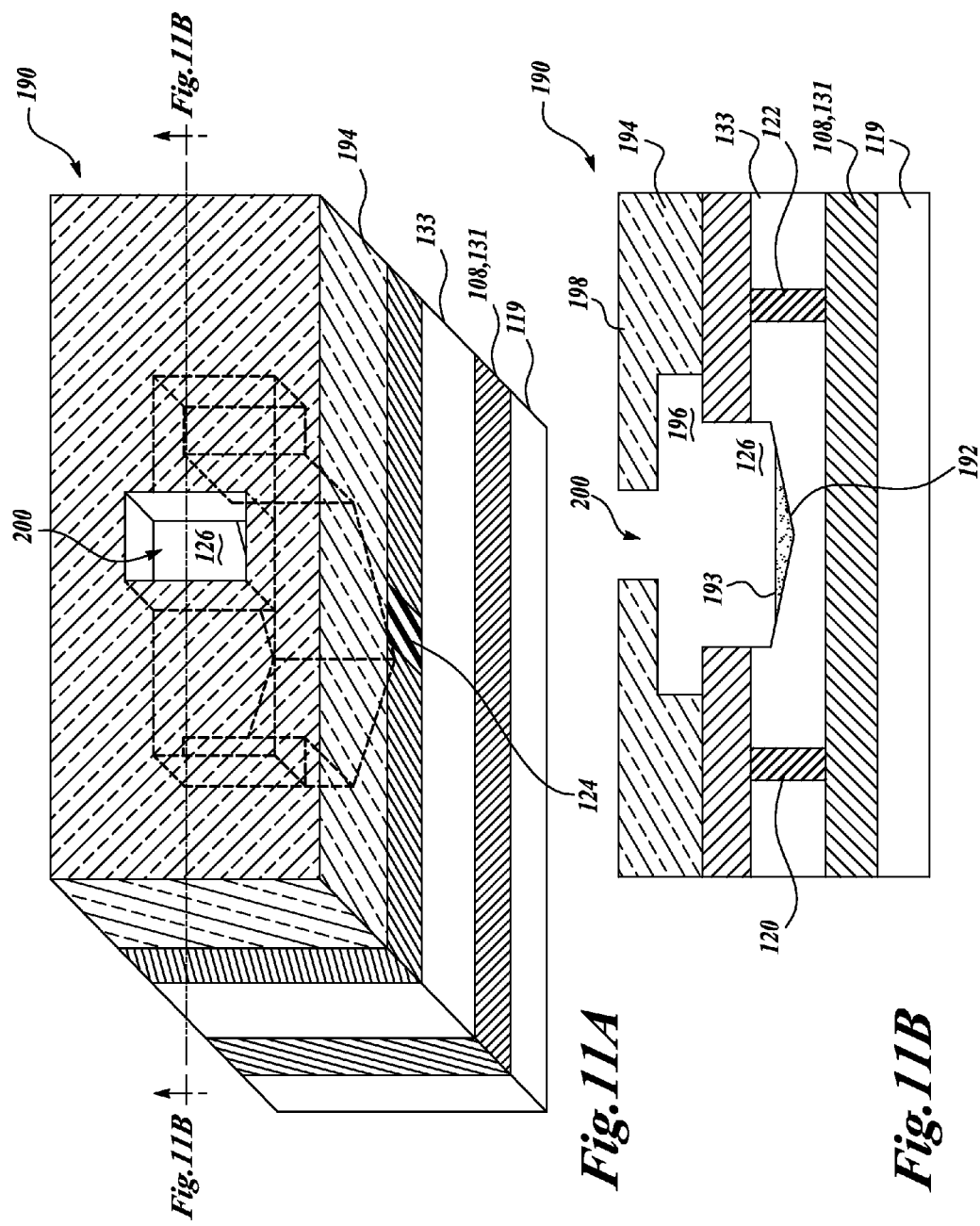
FIG. 11A is a top perspective view of an integrated circuit embodiment of a microfluidic ejection system as described herein.
FIG. 11B is a cross-sectional view of the microfluidic ejection system shown in FIG. 9A, taken along the vertical cut line A-A'.

FIGS. 11A and 11B show a top plan view and a cross-sectional view, respectively, of a microfluidic ejection system 190 according to one embodiment as described herein. The microfluidic ejection system 190 includes elements of the microelectronic fluid sensor 104a described above, including the high resistance material 131 used as the reference device 108, the electrodes 120 and 122, the second insulator 124, and the fluid reservoir 126.

In the microfluidic ejection system 190, the lower boundary of the fluid reservoir 126 further includes a depression 192 that allows a small volume of fluid 193 to be captured on the bottom of the reservoir while remaining isolated from the electrodes 120 and 122. In addition, the microfluidic ejection system 190 further includes an encapsulant 194 on top of the electrodes, the encapsulant enclosing a chamber 196 located directly above the reservoir 126. The chamber 196 is then substantially enclosed by a cap 198. In the embodiment shown in FIG. 10B, the encapsulant 194 and the cap 198 are both made of the same flexible insulating material, which can be a polymer or a dielectric.

The cap 198 includes a nozzle 200 substantially vertically aligned with the depression 192, through which fluid in the reservoir 126 can be ejected in response to a signal from a controller, for example, the microprocessor 168. Following ejection of fluid, the reservoir 126 can be refilled via microfluidic channels from a fluid supply external to the microfluidic ejection system 190.

Figure 12:
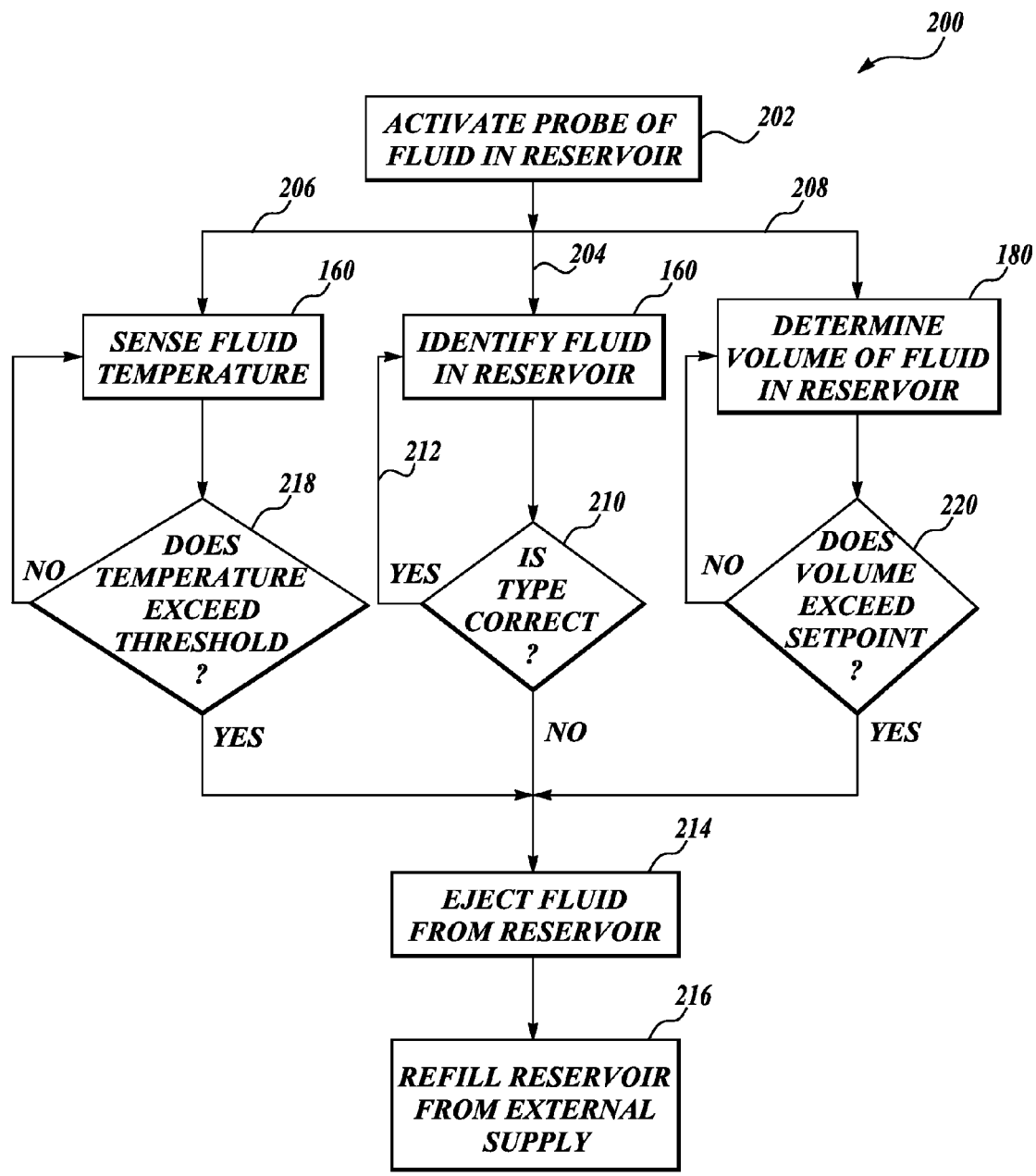
FIG. 12 is a flow diagram showing three alternative methods of operation of the microfluidic ejection system shown in FIGS. 11A and 11B.

FIG. 12 illustrates an exemplary method 200 of operating the microfluidic ejection system 190 that can be carried out by a controller such as the microprocessor 168, for example. The basic operation of the microfluidic ejection system 190 as shown includes a probe to obtain information about the fluid in the reservoir, to determine whether or not to eject the fluid and refill the reservoir, or to allow the fluid to remain in the reservoir.

At 202, a probe of the fluid in the reservoir 126 is activated to determine information about the fluid sample using the resistive fluid detector 104 within the microfluidic ejection system 190. For example, at 204, the type of fluid is verified; at 206, the fluid temperature is sensed and evaluated; and at 208 the volume of fluid in the reservoir 126 is determined and evaluated. Each of these determinations is described in further detail below.

At 204, if the fluid in the reservoir 126 is not known, a fluid verification method can be executed to identify the fluid and decide whether or not to clear the reservoir 126. First, the fluid is identified using the method 160 described above.

At 210, it is determined whether or not the fluid present in the reservoir matches a desired fluid that is expected to be present.

At 212, if the desired type of fluid is present, the identification method 160 can be repeated continuously or periodically to automatically monitor the fluid sample for compositional changes.

At 214, if the fluid is not the correct type of fluid, for example, if the expected fluid is a whole blood sample, while measured sample has a different resistivity that matches blood plasma, fluid can be ejected from the reservoir.

At 216, the reservoir can be re-filled from an external supply. To do this, the microprocessor 168 can send a signal to the external supply to release a sample into a microfluidic channel for delivery into the fluid reservoir 126.

In parallel with identification of the fluid in the reservoir, a thermal actuation method 206 can be executed to monitor the fluid temperature and, in response to changes in the temperature, clear the reservoir 126.

First, the fluid temperature is sensed using the method 160 described above to measure resistivity. At step 172 of the method 160, instead of interpreting the resistivity as a particular type of fluid, the resistivity can be correlated to a fluid temperature.

At 218, it is determined whether or not the fluid tempera- ture exceeds a maximum or a minimum threshold temperature. If the threshold is not exceeded, the method 160 can be repeated continuously or periodically to automatically monitor the fluid sample for changes. It is noted that heat dissipated by the reference device 108 can be a source of thermal excitation of the fluid under test within the reservoir 126.

At 214, if the temperature of the fluid sample is not within a desired range, some or all of the fluid can be ejected from the reservoir 126.

At 216, the reservoir 126 can be re-filled from an external supply.

Additionally or alternatively, a volume actuation method 208 can be executed to adjust the volume of fluid in the reservoir 126.

First, the fluid volume is measured using the method 180 described above.

At 220, it is determined whether or not the volume of the fluid present in the reservoir 126 exceeds a volume setpoint. If the setpoint is not exceeded, the method 180 can be repeated continuously or periodically to automatically monitor the fluid volume for changes.

At 214, if the volume of the fluid sample exceeds the setpoint, some or all of the fluid can be ejected from the reservoir 126. The reference device 108 can be pulsed so as to effectively trigger a thermally-induced fluid ejection at regular intervals.

At 216, the reservoir 126 can be refilled with fresh fluid from an external supply. Alternatively, a user can be alerted to supply a fresh fluid sample instead of feeding the reservoir from an external supply.

By executing one or more of the methods 202, 204, and 206, it is possible to monitor fluid samples for quality, or to perform an electrolytic verification analysis of the fluid sample prior to performing other biological or chemical testing. Such monitoring can also detect errors in sample preparation so as to reduce the number of false negative results obtained by subsequent biochemical testing using an incorrect sample, or an insufficient volume of the sample. Based on the results of monitoring, if the fluid sample fails to meet standards and is ejected, a message can be displayed or transmitted to a user to communicate the status of the sample. Furthermore, monitor data can be recorded in the memory 169 for subsequent statistical analysis. In addition, a fluid sensor that contains a reservoir and an ejection mechanism can be re-usable as opposed to disposable.

So, in addition to the improved form factor that a sensor reservoir offers over that of an impregnated sensor strip, it has been demonstrated herein that an integrated resistive sensor can be significantly more useful than an integrated capacitive sensor. In general, more information can be gathered by the resistive sensor and, furthermore, such additional information can be used to control operation of the sensor itself.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary, to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A microelectronic fluid detector, comprising:
   a substrate;
   a high resistance material on the substrate;
   a first insulator on the high resistance material; and
   a pair of electrodes on the first insulator, the pair of electrodes electrically coupled to the high resistance material;
   a second insulator on the first insulator, the pair of electrodes laterally spaced apart from one another by the second insulator; and
   a reservoir having sidewalls and a base, the sidewalls formed by the pair of electrodes and the second insulator, the base formed by the first insulator.

2. The microelectronic fluid detector of claim 1 wherein the base of the reservoir contains a depression that permits a small volume of fluid accumulated in the depression to remain isolated from the electrodes.

3. The microelectronic fluid detector of claim 1, further comprising a cap over the reservoir, the cap having an opening therein.

4. The microelectronic fluid detector of claim 3 wherein the cap is made of a flexible material that includes one or more of a polymer or a dielectric.

5. The microelectronic fluid detector of claim 3, further comprising an encapsulant between the pair of electrodes and the cap.

6. The microelectronic fluid detector of claim 5 wherein the encapsulant is made of a material that includes one or more of a metal, a polymer, or a thermal oxide.

7. A method of making a microelectronic fluid detector, the method comprising:
   forming a high resistance material on a substrate;
   forming a first insulator on the high resistance material;
   forming a pair of electrodes on the first insulator, the pair of electrodes electrically coupled to the high resistance material;
   forming a second insulator on the first insulator, the pair of electrodes laterally spaced apart from one another by the second insulator; and
   forming a reservoir having sidewalls and a base, the sidewalls formed by the pair of electrodes and the second insulator, the base formed by the first insulator.

8. The method of claim 7, further comprising forming vias in the first insulator.

9. The method of claim 8, wherein the forming of the pair of electrodes include:
   forming a metal layer on the first insulator, the metal layer being electrically coupled to the high resistance material by the vias; and
   removing a first portion of the metal layer to form the pair of electrodes.

10. The method of claim 9, wherein the forming of the reservoir includes removing a second portion of the metal layer to create the reservoir.

11. A microelectronic fluid detector, comprising:
    a substrate;
    a high resistance material on the substrate;
    a first insulator on the high resistance material; and
    a pair of electrodes on the first insulator, the pair of electrodes electrically coupled to the high resistance material;

a second insulator on the first insulator, the pair of electrodes laterally spaced apart from one another by the second insulator; and a reservoir having sidewalls and a base, the sidewalls formed by the pair of electrodes and the second insulator, the base formed by first insulator, each of the pair electrodes including a portion that extends through the first insulator and is in electrical contact with the high resistance material.

12. The microelectronic fluid detector of claim 11, wherein the portion that extends through the first insulator is positioned lateral to the first insulator.

13. A method of making a microelectronic fluid detector, the method comprising:

forming a high resistance material on a substrate;

forming a first insulator on the high resistance material; and forming a pair of electrodes on the first insulator, the pair of electrodes electrically coupled to the high resistance material;

forming a second insulator on the first insulator, the pair of electrodes laterally spaced apart from one another by the second insulator; and forming a reservoir having sidewalls and a base, the sidewalls formed by the pair of electrodes and the second insulator, the base formed by first insulator, each of the pair of electrodes including a portion that extends through the first insulator and is in electrical contact with the high resistance material.

14. The method of claim 13, further comprising:

forming a depression in the base of the reservoir;

forming an encapsulant on top of the pair of electrodes, the encapsulant substantially enclosing a chamber directly above the depression; and covering the chamber with a cap.

15. The method of claim 14 wherein the cap is made of a flexible material, and further comprising forming a nozzle through which fluid in the reservoir can be ejected.

16. The method of claim 13, further comprising:

forming trenches in the first insulator;

filling the trenches with a first metal layer;

depositing a second metal layer in contact with the first metal layer;

removing a first portion of the second metal layer to form the pair of electrodes having a space therebetween;

filling the space with the second insulator; and removing a second portion of the second metal layer to form the reservoir, the reservoir having a floor formed by the first insulator.

17. A microfluidic ejection system, comprising:

a substrate;

a high resistance material on the substrate;

a first insulator in contact with the high resistance material;

a pair of electrodes on the first insulator, the pair of electrodes electrically coupled to the high resistance material;

a second insulator on the first insulator, the pair of electrodes laterally spaced apart from one another by the second insulator; and a reservoir having sidewalls and a base, the sidewalls formed by the pair of electrodes and the second insulator, the base formed by the first insulator;

an encapsulating layer on the pair of electrodes; and a cap on the encapsulating layer, the cap having a fluid ejection nozzle.

18. The system of claim 17 wherein the base of the reservoir includes a depression configured so as to cause a small amount of fluid present in the depression to remain isolated from the electrodes.

19. A device, comprising:

a substrate;

a resistive layer on the substrate;

a first insulating layer on the resistive layer;

a first electrode and a second electrode on the first insulating layer;

a second insulating layer on the first insulating layer, the first electrode being separated from the second electrode by the second insulating layer; and a reservoir having sidewalls formed by the first electrode, the second electrode, and the second insulating layer.

20. The device of claim 19, further comprising first and second vias in the first insulating layer, the first via electrically coupling the first electrode to the resistive layer, the second via electrically coupling the second electrode to the resistive layer.

21. The device of claim 20, wherein the reservoir is positioned between the first via and the second via.

22. The device of claim 19, wherein the reservoir extends in to a portion of the first insulating layer.

23. The device of claim 19, wherein the resistive layer has a resistance of 10-100 kΩ.

24. The device of claim 19, wherein the first electrode is separated from the second electrode by the first insulating layer.

25. The device of claim 19, wherein the first electrode and the second electrode are in electrical contact with the resistive layer.

26. A device, comprising:

a substrate;

a resistive layer on the substrate;

a first insulating layer on the resistive layer;

a first electrode and a second electrode on the first insulating layer, the first electrode and the second electrode electrically coupled to the resistive layer; and a reservoir positioned between the first electrode and the second electrode, the reservoir extends through the first electrode and the second electrode, and in to the first insulating layer.

27. The device of claim 26, further comprising a second insulating layer on the first insulating layer, the first electrode being spaced from the second electrode by the second insulating layer.

28. The device of claim 26, further comprising a first conductive via and a second conductive via in the first insulating layer, the first electrode and the second electrode being electrically coupled to the resistive layer by the first conductive via and the second conductive via, the reservoir being positioned between the first conductive via and the second conductive via.

* * * * *